United States Patent

Humphrey

[11] Patent Number: 5,124,460
[45] Date of Patent: Jun. 23, 1992

[54] ENANTIOSELECTIVE SYNTHESIS OF 3-SUBSTITUTED 1-AZABICYCLO (2.2.1)HEPTANES

[75] Inventor: Guy R. Humphrey, Bell Mead, N.J.

[73] Assignee: Merck Sharp & Dohme Ltd., Hertfordshire, England

[21] Appl. No.: 696,391

[22] Filed: May 6, 1991

[51] Int. Cl.$^5$ .......................... C07D 487/08
[52] U.S. Cl. .................. 548/131; 548/132; 548/133; 548/129; 548/130; 548/543
[58] Field of Search ............... 548/543, 129, 130, 131, 548/132, 133

[56] References Cited

U.S. PATENT DOCUMENTS 4,968,691 11/1990 Orlek .................................. 514/305

FOREIGN PATENT DOCUMENTS

| 239309 | 3/1987 | European Pat. Off. |
| 307142 | 9/1988 | European Pat. Off. |
| 323864 | 1/1989 | European Pat. Off. |
| 301729 | 2/1989 | European Pat. Off. |
| 307140 | 3/1989 | European Pat. Off. |
| 0398629 | 5/1990 | European Pat. Off. |

OTHER PUBLICATIONS

Chem. Letter (1986), 839 et seq.

Primary Examiner—David B. Springer
Attorney, Agent, or Firm—Charles M. Caruso; Manfred Polk

[57] ABSTRACT

A process for preparing a substantially pure enantiomer of a compound formula (I)

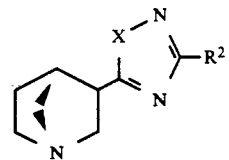

wherein
X is O or S; and
$R^2$ represents hydrogen, —CF$_3$, —OR$^7$, —SR$^7$, —NR$^7$R$^8$, —CN, —COOR$^7$, —CONR$^7$R$^8$, or a saturated or unsaturated, substituted or unsubstituted hydrocarbon group, wherein $R^7$ and $R^8$ are independently selected from hydrogen and C$_{1-2}$alkyl provided that —NR$^7$R$^8$ is other than NH$_2$;

which process comprises cyclization of a compound of formula (10) or salt thereof:

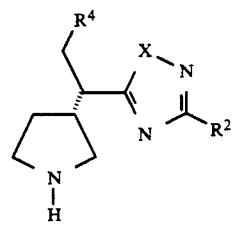

wherein X and $R^2$ are as defined in formula (I); and $R^4$ is a labile leaving group and optionally epimerizing the endo-diastereomer so prepared to produce the corresponding exo-diastereomer.

8 Claims, No Drawings

ENANTIOSELECTIVE SYNTHESIS OF 3-SUBSTITUTED 1-AZABICYCLO (2.2.1)HEPTANES

The present invention relates to a process for resolving enantiomers of compounds having muscarinic agonist activity.

In European published patent specifications nos. 239309, 301729, 307142, 307140, 323864 and 261763 are disclosed certain azabicyclic compounds, including oxa- and thia- diazole derivatives thereof, having, for example, muscarinic agonist activity and processes for their preparation. The processes disclosed are multi-step and include those which proceed via intermediates of formula (A)

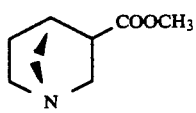

(A)

including analogues and derivatives thereof. Both the final azabicyclic compounds and the intermediates of formula (A) have at least two asymmetric centres and can therefore exist as both enantiomers and diastereomers. Some, such as the intermediate of formula (A), can exist as exo- and endo- isomers. However, no process is disclosed wherein the optical isomers of the final azabicyclic compounds (nor the intermediates of formula (A) nor its analogues and derivatives) can separately be prepared or the racemic mixture resolved Thus, in order to prepare individual enantiomers of the oxa- and thia- diazoles mentioned above and other substituted azabicycles, attempts were made to resolve optically active intermediates used in their preparation. Various of the conventional methods were tried, but without complete success. For example, it was found that using chiral acids such as tartaric and camphor-10-sulphonic was unsuccessful. Likewise, the use of chiral esters such as derivatives of menthol, N-benzoyl-2-amino-1-butanol and N-benzoyl norephedrine did not work as either they could not be prepared or the chiral derivatives of the azabicycles would not separate. It was then surprising to find a new stereoselective process, starting with a commercially-available, optically active compound which could be used to prepare the desired final enantiomers without undertaking a resolution step. Thus the present invention provides a process for preparing a substantially pure enantiomer of a compound of formula (I)

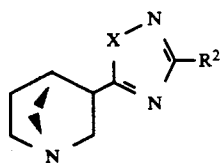

(I)

wherein X is O or S; and
$R^2$ represents hydrogen, $-CF_3$, $-OR^7$, $-SR^7$, $-NR^7R^8$, $-CN$, $-COOR^7$, $-CONR^7R^8$, or a saturated or unsaturated, substituted or unsubstituted hydrocarbon group, wherein $R^7$ and $R^8$ are independently selected from hydrogen and $C_{1-2}$ alkyl provided that $-NR^7R^8$ is other than $NH_2$;

which process comprises cyclisation of a compound of formula (10) or salt thereof:

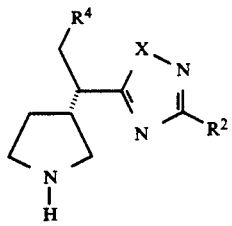

(10)

wherein
X and $R^2$ are as defined in formula (I); and
$R^4$ is a labile leaving group such as mesylate (OS-$(O)_2CH_3$), lower alkanoate such as acetate or halo such as chloro or bromo
and optionally, if desired, epimersing the endodiastereomer so prepared to produce the corresponding exodiastereomer.

Cyclisaton of (10) is carried out in a pH range of from 6 to 10, such as in a two-phase system comprising a non-aqueous phase and a mild inorganic base such as an aqueous alkali or alkaline earth metal carbonate, hydrogencarbonate or hydroxide such as sodium or potassium carbonate or hydrogencarbonate or barium hydroxide; preferably aqueous sodium carbonate The non-aqueous phase is any in which the compound of formula (I) so prepared is soluble, for example, a lower alkanol or ester such as t-butanol or ethylacetate, or an ether such as diethyl ether, or toluene For a single-phase system, any alcohol and water can be used, for example t-butanol/water.

The compound of formula (10) is usually in a salt form such as the trifluoroacetate salt as it is prepared by deprotecting the corresponding compound of formula (9):

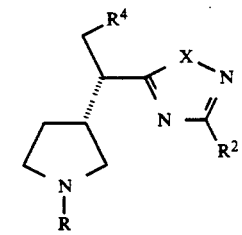

(9)

wherein X, $R^2$ and $R^4$ are as defined in formula (10); and
R is a secondary amine blocking group which is removable under mild conditions. Suitable blocking or protecting groups are known to those skilled in the art and include t-butoxycarbonyl or benzyloxycarbonyl.

Removal of the blocking group R to form compound (10) is carried out by conventional techniques known to those skilled in the art, for example, by reaction with trifluoroacetic acid or a hydrogen halide such as hydrogen bromide or hydrogen chloride. For this purpose, the reaction is preferably carried out in solution in a suitable solvent such as t-butanol, or a lower alkyl organic acid or ester such as acetic acid, or ethyl or isopropyl acetate.

The compound of formula (9) may be prepared by conventional techniques from the corresponding hydroxy analogue of formula (8):

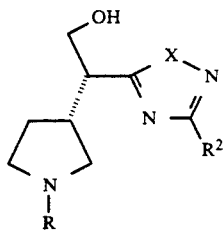

(8)

wherein
X, R and $R^2$ are as defined in formula (9).

Conversion of the hydroxy group in the alcohol (8) for a suitable leaving group $R^4$ to form (9) may be accomplished by methods analogous to those known in the art. For example, mesylation ($R^4$=OS(O)$_2$CH$_3$) can take place by addition of methanesulphonyl chloride to the alcohol (8) in a suitable inert organic solvent such as ethyl acetate under cooling in the presence of a lower alkyl amine such as triethylamine When $R^4$ is halo, bromination may be undertaken by phosphorous tribromide or chlorination by thionyl chloride in a solvent such as an ether or tetrahydrofuran. Optionally, the mesylate may be formed first and then converted to halo. Indeed, any leaving group may be converted to any other suitable leaving group by conventional methods.

The alcohol (8) is itself prepared by reduction of the corresponding ester of formula (7):

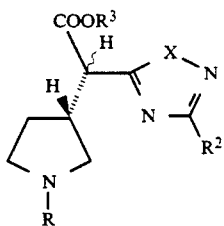

(7)

wherein
X, R and $R^2$ are as defined in formula (8); and
$R^3$ is lower alkyl or benzyl.

The pyrrolidine ester (7) is reduced to the alcohol (8) by a conventional mild reducing agent such as by sodium borohydride in the presence of methanol in an inert organic solvent such as tetrahydrofuran or an ether under an inert atmosphere such as nitrogen, preferably at a reduced temperature of about $-10°$ to $0°$ C., preferably $-5°$ to $0°$ C.

The pyrrolidine ester (7) is prepared by reaction of the heterocyclyl ester (6) with the protected pyrrolidine (3):

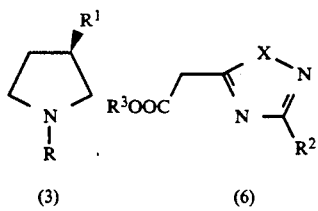

wherein
R, $R^2$ and $R^3$ are as defined in formula (7); and
$R^1$ is a labile leaving group such as mesylate, lower alkanoate or p-toluenesulphonate.

The reaction may be undertaken in typical alkylation conditions such as in the presence of a base such as sodium hydride, potassium t-butoxide or diazabicyclo[5.4.0]undec-7-ene (DBU), optionally in a solvent such as tetrahydrofuran, dimethylformamide, toluene or 1,3-dimethyl-3,4,5,6-tetrahydro-2(1H)-pyrimidinone (DMPU). Preferably DBU in DMPU is used. The reaction may be carried out at elevated temperatures such as in the range of from 60° to 100° C., preferably around 60° C. Preferably, an inert atmosphere such as nitrogen is used.

The protected pyrrolidine (3) may be prepared from alcohol (2) by methods similar to those described in relation to (9). In the case where $R^1$ is p-tosylate, the reaction can be undertaken by p-toluenesulphonyl chloride at slightly elevated temperatures.

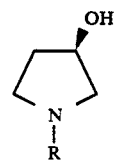

(2)

The alcohol (2) may itself be prepared by conventional techniques for protecting secondary amines such as by addition of (R)$_2$O where R is as defined in formula (2), preferably di-tert-butyldicarbonate, but agents such as benzylchloroformate may also be used. The addition is preferably undertaken in aqueous base such as an aqueous inorganic base e.g. a carbonate, hydroxide or hydrogen carbonate e.g. aqueous sodium hydrogen carbonate or an organic base such as triethylamine or DBU. The protection is preferably carried out on an easy-to-handle salt of the alcohol (1) where it is desired to isolate the compound before protecting it. Otherwise, the starting compound L-trans-4-hydroxyproline may be decarboxylated and the resulting alcohol (1) blocked in situ. Thus, the compound of formula (2) is prepared by protecting the compound of formula (1) or a salt thereof.

Decarboxylation of commercially available (2S, 4R)-(−)-4-hydroxy-2-pyrrolidine carboxylic acid (L-transhydroxyproline) to give the hydrochloride salt of (3R)-3-hydroxypyrrolidine (1) is known from Chem. Lett. (1986), 893 et. seq. Other salts may be prepared in analogous fashion, for example, by addition of the corresponding acid, preferably maleic acid, after reaction of L-transhydroxyproline with a decarboxylating agent such as 2-cyclohexen-1-one. The decarboxylation may be undertaken in a suitable inert solvent such as cyclohexanol at the reflux temperature of the reaction mixture.

The heterocyclic ester (6) is prepared by methods analogous to those known to those skilled in the art. For example, when X is O and $R^2$ is —CF$_3$, —CONR$^7$R$^7$, or a saturated or unsaturated, substituted or unsubstituted hydrocarbon substituent, (6) may be prepared by reaction of a compound of formula (5) with a compound of formula (11)

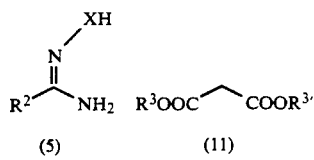

wherein $R^2$ and $R^3$ are as defined in formula (6); and $R^{3'}$ is the same as $R^3$ or a different lower alkyl or benzyl group. The compound of formula (11) is preferably diethylmalonate and the reaction is preferably undertaken in an inert, organic solvent with a boiling point in the range of from 100° to 140° C. such in toluene or xylene.

The compound of formula (5) is prepared from the cyanide $R^2CN$ (4) as described in, for example, European patent specification No. 239309. For example, by reaction with hydroxylamine or a salt thereof such as the hydrochloride in the presence of sodium or potassium carbonate, preferably in a polar organic solvent such as an alcohol e.g. methanol under an inert atmosphere such as nitrogen.

Throughout this specification "lower alkyl" signifies $C_{1-4}$ alkyl groups having straight or branched, saturated chains. Preferably, $R^2$ throughout is a $-CF_3$ group or a saturated or unsaturated, substituted or unsubstituted hydrocarbon group; more preferably having from 1 to 6 carbon atoms. Especially preferred is when $R^2$ is $-CF_3$ or a $C_{1-6}$ saturated hydrocarbon such as $C_{1-6}$ straight or branched chain alkyl, for example methyl or ethyl or cycloalkyl, for example cyclopropyl or cyclopropylmethyl. Preferably, X is O.

In any of the above reactions it may be necessary and/or desirable to protect any sensitive groups in the compounds. The protecting groups may be removed at any convenient stage in the synthesis of the desired compound according to conventional techniques.

The present invention therefore further provides novel intermediates of formulae (7), (8), (9) and (10) as defined above, which may be represented by formula (B):

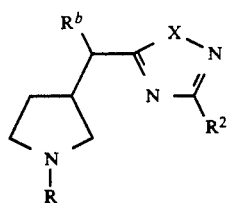

wherein

X and $R^2$ are as defined in formula (I);

R is hydrogen or a secondary amine blocking group which is removable under mild conditions; and $R^b$ is a group $COOR^3$ (where $R^3$ is lower alkyl or benzyl, OH, or a labile leaving group, and methods for their preparation, and intermediates of formula (3) and (6) and methods for their preparation.

The final product of formula (I) may further be treated to give the desired enantiomer or a mixture thereof. For example, the exo- isomer may be separated from an exo/endo mixture by chromatography. The mixture may then be epimerised to increase the yield of the exoisomer.

The present invention will now be illustrated by the following example, although other ways of putting it into effect will be clear to the person skilled in the art.

EXAMPLE 1

(3R,4R)-3-(3-Cyclopropyl-1,2,4-oxadiazol-5-yl)-1-azabicyclo [2.2.1]heptane

[The numbers in the titles refer to those in Scheme 2]

A. Preparation of (3R)-3-Hydroxypyrrolidine (1) Hydrogen Maleate

A 20 liter flange flask equipped with mechanical stirrer, thermometer, nitrogen inlet and condenser, was charged with trans L-hydroxyproline (Degussa, 1.00 kg, 7.63 Mol), cyclohexanol (Aldrich 30818, 5.0 l) and 2-cyclohexen-1-one (Lancaster, 100 ml). The slurry was stirred and heated at vigorous reflux (−155° C.) until complete solution was observed (5.5 h). The clear red solution was cooled to 25 C and maleic acid (885 g, 7.63 Mol) added in portions over 30 min. The reaction temperature was maintained at 30°-35° C. during addition On complete addition, crystallisation occurred and the slurry was aged at 25° C. for 30 min. Ethyl acetate (10.0 l) was added dropwise over 1 h and the resultant slurry allowed to age at room temperature for 2 h. The slurry was filtered, the cake washed with ethyl acetate/cyclohexanol (2/1, 3.0 l), ethyl acetate (3.0 l), and dried in vacuo at 20° C. overnight.

B. Preparation of (3R)-N-(t-Butoxycarbonyl)-3-hydroxypyrrolidine (2)

A 10 gallon glass-lined vessel was charged with water (29 l) and sodium bicarbonate (7.42 kg, 88.3 Mol). To the resultant stirred slurry, at 20° C., was added a solution of (3R)-3-hydroxypyrrolidine hydrogen maleate (1) (3.60 kg, 17.7 Mol) in Water (10.8 l), over 15 min (effervescence). On complete addition, di-tertbutyldicarbonate (Fluka, 4.64 kg, 21.3 Mol) was added in one portion (no exotherm noted) The slurry was vigorously stirred over the weekend (i.e. total −65 h) Ethyl acetate (10 l) was added and the mixture filtered to remove suspended solids The aqueous layer was separated and re-extracted with ethyl acetate (10 l). The combined organics were dried ($Na_2SO_4$) and evaporated under reduced pressure to give a colourless oil.

C. Preparation of (3R)-N-(t-Butoxycarbonyl)-3-methanesulphonyloxypyrrolidine (3)

A dry 10 gallon glass-lined vessel was charged with the alcohol (2) (3.39 kg d.b., 18.1 Mol) and ethyl acetate (50 l) under nitrogen. The solution was cooled to −5° C. and triethylamine (Lancaster B/N 076337, 5.1 l) was added in one portion. Methanesulphonyl chloride (Lancaster B/N 79561, 1.68 l, 21.7 Mol) was added dropwise over 1 h, maintaining the reaction temperature at −5°-2° C. On complete addition, the slurry was aged at −5° C. for 30 min. Water (20 l) was added over 10 min and the phases well mixed The aqueous layer was separated and the organics washed with 1M aqueous hydrochloric acid (10 l), saturated sodium bicarbonate (10 l) and dried ($Na_2SO_4$). Solvent evaporation gave the product as a pale yellow oil.

D. Preparation of Cyclopropylcarboxamide Oxime (5)

A 20 gallon glass-lined vessel was charged with methanol (32 l), hydroxylamine hydrochloride (Lancaster, 3.88 kg, 55.8 Mol) and cyclopropyl cyanide (Fluka BN 533321, 4.50 kg, 5.01 l, 67.1 Mol) under a nitrogen atmosphere. A solution of potassium carbonate (7.72 kg, 55.9 Mol) in water (28 l) was added dropwise with stirring over 20 min. Effervescence and a slight exotherm (15° to 20° C.) was noted. After complete addition the stirred mixture was warmed to 70° C.±2° C., to maintain a slight reflux, for 18 h. The reaction mixture was cooled to 55° C. and the solvents distilled under reduced pressure to a residual volume of −20 l. The residue was transferred to a 20 l Buchi apparatus and the remaining solvents removed. The oily-solid residue was swished in THF (10 l) and filtered. The cake was washed with THF (10 l) and the filtrates dried (Na$_2$SO$_4$). Evaporation of solvents gave a colourless oil which solidified on standing at −b 5° C.

E. Preparation or Ethyl 2-(3-cyclopropyl-1,2,4-oxadiazol-5-yl)acetate (6)

A 20 gallon glass-lined vessel was charged with cyclopropylcarboxamide oxime (5) (5.39 kg, 53.9 Mol), toluene (Shell Chem, 324, 54.0 l) and diethylmalonate (Lancaster B/N 52068785, 24.5 kg, 160 Mol) under nitrogen at room temperature. The stirred reaction mixture was heated at gentle reflux for 21 h. The ethanol/water produced during the reaction was periodically drawn off to maintain a high reflux temperature (i.e 105°-110° C.) The reaction mixture was cooled to room temperature, washed with 25% saturated brine (3×5 l) and the toluene removed under reduced pressure. The residue was distilled using a small fractionating column to give: a) recovered diethylmalonate b.p. 60°-70° C. at 2 mbar; and b) oxadiazole-ester (6) b.p. 90°-120° C., at ~2 mbar.

F. Preparation of (2S,3'R) and (2R,3'R) Ethyl-2-(3-cyclopropyl-1,2,4-oxadiazol-5-yl)-2-[N-(t-butoxycarbonyl)pyrrolidin-3-yl)acetate (7)

A 20 liter flange flask fitted with mechanical stirrer, nitrogen inlet and addition funnel was charged with the ester (6) (6.24 kg, 31.8 Mol) and mesylate (3) (4.22 kg, 15.9 Mol). Diazabicyclo[5.4.0]undec-7-ene (Fluka B/N 538856, 4.60 kg, 30.2 Mol) was added dropwise to the stirred mixture, at 20° C., over 20 min (an exotherm to 45° C. was noted) The resultant solution was heated (temperature controlled water bath) to 54°±1° C. for 30 hours. The reaction mixture was cooled to 20° C. and partitioned between ethyl acetate (12.5 l) and 1N hydrochloric acid (8 l). The organic layer was separated and washed with 1M hydrochloric acid (4 l), 50% saturated brine solution (2×5 l) and dried Na$_2$SO$_4$. Evaporation of solvents under reduced pressure gave a red oil. The crude oil was passed down a short path distillation apparatus at 130° C. and 0.4–0.7 mmHg to remove the excess ester (6) and pyrrolidine (3). A red, viscous, residual oil was obtained and used 'as is' in the following reduction step.

G. Preparation of (2S,3'R) and (2R,3'R) 2-(3-Cyclopropyl-1,2,4-oxadiazol-5-yl)-2-N-(t-butoxycarbonyl)pyrrolidin-3-yl]ethanol (8)

To a stirred solution of alkylated ester (7) (6.20 kg, 15.99 Mol) in dry THF (Fisons B/N 14288129, 18.6 l) at −5° C., under nitrogen, was added sodium borohydride (Lancaster, 2.57 kg, 67.9 Mol) portionwise maintaining the reaction temperature ~ −5° C. Methanol (13.8 l) was added dropwise over 1 h maintaining reaction temperature −5°-0° C. On complete addition, the reaction was stirred at −5° C. for a further 3 h. TLC (Ether/Silica) showed complete consumption of starting material. The reaction mixture was cooled to −20°C. (to avoid over-reduction) and added, via a cannula, to a stirred mixture of ethyl acetate (30 l) and 2N hydrochloric acid (146 l) at −10° to −5° C. The quench temperature was maintained by addition of solid carbon dioxide. On complete addition, the stirred mixture was aged for 15 minutes at <0° C. and then allowed to settle. The aqueous layer was separated, and re-extracted with ethyl acetate (5×15 l). The organics were combined, washed with 2% hydrochloric acid (13 l), saturated brine (3×13 l) and dried (Na$_2$SO$_4$). The solvent was evaporated to give the alcohols (8) as a dark oil.

H. Preparation of Methanesulphonate Esters (9)

A 20 gallon glass-lined vessel was charged with alcohol (8) (4.6 kg, 12.2 Mol) and ethyl acetate (Alcohols Ltd., B/N 21189, 46 l). The solution was cooled to −20° C. using internal, liquid nitrogen cooling and triethylamine (Lancaster, O/N 076337, 3.97 l, 28.4 Mol) added over 10 min. Methanesulphonylchloride (Lancaster, B/N 91466-00-474, 1.32 l, 17.1 Mol) was added slowly over 0.5h maintaining the reaction temperature between −20° and −15° C. On complete addition the reaction was aged at −20° C. for 0.75h. 2N Hydrochloric acid (14.4 l) was added dropwise, allowing the reaction temperature to rise to −10° C. The lower aqueous layer was removed and reextracted with ethyl acetate (3×3.0 l). The combined organics were washed with saturated brine solution (4×6.4 l), concentrated to 10 l, filtered and the remaining solvent evaporated (Buchi) to leave a dark oil (unstable to GC/MS).

I. Preparation of (3S, 4R) and (3R, 4R)-3-(3-Cyclopropyl-1,2,4-oxadiazol-5-yl)-1-azabicyclo[2.2.1]heptane To a solution of the methanesulphonate esters (9) (5.90 kg, 14.7 Mol) in t-butanol (Fisons B/N 12, 15, 52 and Aldrich B/N 28758, 3.0 l) at room temperature was added trifluoroacetic acid (Fluorochem B/N F07160, Aldrich B/N 33525, 12.0 l) dropwise over 1 h. The reaction temperature was maintained between 20°-25° C. during the addition. After a further 1 h age period, TLC (Ether/Silica) showed no starting material remaining. The reaction mixture was diluted with t-butanol (Aldrich B/N 28758, 24.0l) and 10% aqueous sodium carbonate (−80 l) added to adjust the pH to 7.5. The reaction mixture was heated to 40° C. and the pH maintained constant for 1.5 h by the addition of aqueous carbonate. The pH was raised to 8.5 for 1.5 h and finally increased to 9.5 whereupon the product was extracted into toluene (20.0 l). The aqueous layer was separated and extracted with toluene (4×10 l). The organics were combined and dried (Na$_2$SO$_4$). Evaporation of solvent gave a dark oil. The crude product was purified by chromatography on silica gel (Merck Kieselgel 60, ART 7734, B/N TA 534034 50 kg) using first ethyl acetate/methanol (5/1 l) then methanol to elute the endo isomer. Pure exo isomer free base along with an endo/exo mixture was obtained. To a solution of the free base exo/endo mixture (10.0 g) in IMS (20 ml) was added a solution of potassium t-butoxide (1.0 g) in IMS (30 ml). The solution was heated at gentle reflux for 30 min. The epimerisation was generally complete after this period. The reaction mixture was extracted with ethyl acetate (2×10 ml), the organics combined and dried (Na$_2$SO$_4$). The solvent was evaporated to residue and partitioned between water (15 ml) and ethyl acetate (15 ml). The aqueous layer was evaporated to give an oil, 9.8 g, 98% recovery, ratio of exo:endo (76:24).

EXAMPLE 2

Preparation of (3R,4R)-3-(3-Cyclopropyl-1,2,4-oxadiazol-5-yl)-1-azabicyclo2.2.1]heptane p-toluenesulphonate A solution of p-toluenesulphonic acid monohydrate (109 g, 0.57 Mol) in ethyl acetate (500 ml) was dried by azeotropic distillation (170 ml removed). To the resultant cooled solution was added isopropylalcohol 120 ml). A pre-filtered solution of epimerised free base (exo/endo; 74/26, 118 g, 0.57 Mol) in ethyl acetate (260 ml) and IPA (116 ml) was added at room temperature over 10 min (exotherm to 40° C.). The solution was seeded with pure pTSA salt of the base (−20 mg) and the slurry allowed to age at room temperature for 2 h. The slurry was chilled at 0.5° C. for 1 h, filtered and the cake washed with ethyl acetate (200 ml). The white crystalline solid was dried in vacuo at room temperature, washed in ethyl acetate (10 mlg$^{-1}$l) at reflux for 2 h, cooled to room temperature (1 h), filtered and the cake washed with ethyl acetate (100 ml). The white crystalline solid was dried in vacuo to give pTSA salt m.p. 130°–131° C. (propan-2-ol/ethyl acetate).

What is claimed is:

1. A process for preparing a substantially pure enantiomer of a compound of formula (I)

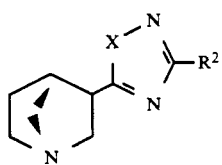

(I)

wherein X is selected from the group consisting of O and S; and $R^2$ is selected from the group consisting of hydrogen, —$CF_3$, —$OR^7$, —$SR^7$, —$NR^7R^8$, —CN, —$COOR^7$, —$CONR^7R^8$ and saturated and unsaturated hydrocarbon groups, wherein $R^7$ and $R^8$ are independently selected from the group consisting of hydrogen and $C_{1-2}$alkyl, provided that —$NR^7R^8$ is other than $NH_2$; said process comprises cyclisation at pH ranging from 6–10 of a compound of formula (10):

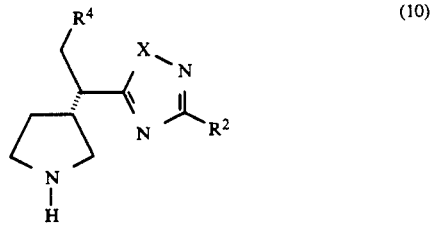

(10)

or salt thereof;

wherein X and $R^2$ are as defined in formula (I); and $R^4$ is a labile leaving group; and optionally converting the endo-diastereomer so prepared to produce the corresponding exo-diastereomer via racemisation.

2. The process according to claim 1, wherein $R^2$ is selected from the group consisting of $CF_3$ and $C_{1-6}$ saturated hydrocarbon.

3. The process according to claim 1, wherein $R^2$ is selected from the group consisted of $CF_3$, methyl, ethyl, cyclopropyl and cyclopropylmethyl.

4. The process according to claim 1, wherein X is O.

5. The process according to claim 1, wherein $R^4$ is mesylate, lower alkanoate or halo.

6. The process according to claim 1, wherein the compound of formula (I) is (3R, 4R)-3-(3-cyclopropyl-1,2,4-oxadiazol-5-yl)-1-azabicyclo[2.2.1]heptane.

7. The process according to claim 1, wherein cyclisation of (10) is carried out in a two-phase system comprising a mild inorganic base and a non-aqueous phase wherein the compound of formula (I) is soluble.

8. The process according to claim 1, wherein the compound of formula (10) is in the form of the trifluoroacetate salt.

* * * * *